United States Patent [19]
Chornenky et al.

[11] Patent Number: 5,854,822
[45] Date of Patent: Dec. 29, 1998

[54] MINIATURE X-RAY DEVICE HAVING COLD CATHODE

[75] Inventors: Victor I. Chornenky, Minnetonka; Dale L. Schreiner, Cologne; Michael R. Forman, Vadnais Heights, all of Minn.

[73] Assignee: XRT Corp., St. Paul, Minn.

[21] Appl. No.: 900,609

[22] Filed: Jul. 25, 1997

[51] Int. Cl.⁶ .................................................. A61N 5/10
[52] U.S. Cl. ............................... 378/122; 378/65; 604/20
[58] Field of Search ............................ 378/64, 65, 68, 378/119, 121, 122, 136; 604/20

[56] References Cited

U.S. PATENT DOCUMENTS

| | | |
|---|---|---|
| Re. 34,421 | 10/1993 | Parker et al. . |
| 1,786,373 | 12/1930 | Walker . |
| 1,881,448 | 10/1932 | Forde et al. . |
| 2,467,812 | 4/1949 | Clapp . |
| 2,766,385 | 10/1956 | Herrnring et al. . |
| 3,005,096 | 10/1961 | Chynoweth . |
| 3,073,960 | 1/1963 | Guentner et al. . |
| 3,125,679 | 3/1964 | Ohde et al. . |
| 3,256,439 | 6/1966 | Dyke et al. . |
| 3,348,051 | 10/1967 | Weighart et al. . |
| 3,381,129 | 4/1968 | Duftschmid . |
| 3,388,314 | 6/1968 | Gould . |
| 3,484,721 | 12/1969 | Bond et al. . |
| 3,508,059 | 4/1970 | Vanderpool . |
| 3,538,919 | 11/1970 | Meyer . |
| 3,564,251 | 2/1971 | Youmans . |
| 3,617,939 | 11/1971 | Bond et al. . |
| 3,628,021 | 12/1971 | MacDonald . |
| 3,691,417 | 9/1972 | Gralenski . |
| 3,714,486 | 1/1973 | McCrary . |
| 3,752,990 | 8/1973 | Fischer . |
| 3,866,050 | 2/1975 | Whitfield . |
| 3,878,394 | 4/1975 | Golden . |
| 3,883,760 | 5/1975 | Cunningham, Jr. . |

(List continued on next page.)

FOREIGN PATENT DOCUMENTS

| | | |
|---|---|---|
| 0 697 712 A1 | 2/1996 | European Pat. Off. . |
| 2054738 | 5/1972 | Germany . |
| 26 08 418 | 9/1977 | Germany . |
| 58-145098 (A) | 8/1993 | Japan . |
| 814331 | 3/1981 | U.S.S.R. . |
| WO 95/20241 | 7/1995 | WIPO . |
| WO 96/02059 | 1/1996 | WIPO . |

OTHER PUBLICATIONS

PCT International Search Report (English Translation Abstract of PCT/US96/13629 included) (4 pages) no date.
Brochure: "Dunlee DL–1 Stationary Anode Insert", Dunlee Corporation, Bellwood, IL 60104, Jun. 1972.
Asano et al., *Jp. J. Appl. Phys.*, 31(Part 1, 9B):3098–3101 (Sep. 1992).
Brady, et al., *Gynecologic Oncology*, 2:314–323 (1974).
Condado, et al., 1 page, *Discoveries in Radiation for Restenosis*, Emory University School of Medicine (Jan. 1996).
Fischell, et al., *Circulation*, 90(6): 2956–2963 (Dec. 1994).
Geissler et al., *Physics Letters A*, 176:387–392 (1993).
Gundel, et al., *Nuclear Instruments and Methods in Physics Research*, A280:1–6 (1989).
Gundel, et al., *J. Appl. Phys.*, 69(2):975–982 (Jan. 1991).
Hehrlein, et al., *Circulation*, 92(6):1570–1575 (Sep. 1995).
March, et al., *Circulation*, 87(1):184–191 (Jan. 1993).
Matsuda, et al., *Journal of Materials Science*, 21:649–658 (1986).

(List continued on next page.)

*Primary Examiner*—David P. Porta
*Attorney, Agent, or Firm*—Merchant, Gould, Smith, Edell, Welter & Schmidt, P.A.

[57] ABSTRACT

Generally, the present invention provides a device for insertion into a body and delivery of x-ray radiation, and a method for fabricating such a device. The device includes a connector, the vacuum housing, an anode and a cathode having a granular surface and being composed of a material that allows it to act as a getter. The cathode may also contain diamond material in one embodiment.

18 Claims, 3 Drawing Sheets

U.S. PATENT DOCUMENTS

| | | |
|---|---|---|
| 3,920,999 | 11/1975 | Drexler et al. . |
| 3,970,884 | 7/1976 | Golden . |
| 3,987,281 | 10/1976 | Hodes . |
| 4,058,486 | 11/1977 | Mallozzi et al. . |
| 4,060,731 | 11/1977 | Rissi . |
| 4,097,759 | 6/1978 | Furbee et al. . |
| 4,104,526 | 8/1978 | Albert . |
| 4,104,530 | 8/1978 | Weiss . |
| 4,104,531 | 8/1978 | Weiss . |
| 4,104,532 | 8/1978 | Weiss . |
| 4,109,154 | 8/1978 | Taumann . |
| 4,117,334 | 9/1978 | Strauts . |
| 4,143,275 | 3/1979 | Mallozzi et al. . |
| 4,158,138 | 6/1979 | Hellstrom . |
| 4,163,901 | 8/1979 | Azam et al. . |
| 4,191,193 | 3/1980 | Seo . |
| 4,315,182 | 2/1982 | Furbee ................................ 378/125 |
| 4,344,181 | 8/1982 | Baecklund . |
| 4,359,660 | 11/1982 | Smith et al. . |
| 4,368,538 | 1/1983 | McCorkle . |
| 4,563,769 | 1/1986 | Madsen . |
| 4,607,380 | 8/1986 | Oliver . |
| 4,625,324 | 11/1986 | Blaskis et al. ...................... 378/130 |
| 4,636,195 | 1/1987 | Wolinksy . |
| 4,646,338 | 2/1987 | Skillicorn . |
| 4,669,467 | 6/1987 | Willett et al. . |
| 4,670,894 | 6/1987 | Birnbach et al. . |
| 4,694,480 | 9/1987 | Skillicorn . |
| 4,701,941 | 10/1987 | Szirmai et al. . |
| 4,702,228 | 10/1987 | Russell, Jr. et al. . |
| 4,715,054 | 12/1987 | Kato et al. . |
| 4,763,671 | 8/1988 | Goffinet . |
| 4,789,997 | 12/1988 | Madsen et al. . |
| 4,794,931 | 1/1989 | Yock . |
| 4,800,581 | 1/1989 | Kujirai et al. . |
| 4,824,436 | 4/1989 | Wolinsky . |
| 4,856,036 | 8/1989 | Malcolm et al. . |
| 4,913,142 | 4/1990 | Kittrell et al. . |
| 4,924,485 | 5/1990 | Hoeberling . |
| 4,966,596 | 10/1990 | Kuntz et al. . |
| 4,976,266 | 12/1990 | Huffman et al. . |
| 4,979,199 | 12/1990 | Cueman et al. . |
| 4,987,007 | 1/1991 | Wagal et al. . |
| 5,042,486 | 8/1991 | Pfeiler et al. . |
| 5,059,166 | 10/1991 | Fischell et al. . |
| 5,077,771 | 12/1991 | Skillicorn et al. . |
| 5,087,244 | 2/1992 | Wolinsky et al. . |
| 5,090,043 | 2/1992 | Parker et al. . |
| 5,099,845 | 3/1992 | Besz et al. . |
| 5,101,422 | 3/1992 | Thiel et al. . |
| 5,106,360 | 4/1992 | Ishiwara et al. . |
| 5,138,220 | 8/1992 | Kirkpatrick . |
| 5,148,463 | 9/1992 | Woodruff et al. . |
| 5,153,900 | 10/1992 | Nomikos et al. . |
| 5,165,093 | 11/1992 | Miller et al. . |
| 5,199,939 | 4/1993 | Dake et al. . |
| 5,222,116 | 6/1993 | Eloff et al. . |
| 5,228,176 | 7/1993 | Bui et al. . |
| 5,264,801 | 11/1993 | Decou, Jr. et al. . |
| 5,290,275 | 3/1994 | Kittrell et al. . |
| 5,313,949 | 5/1994 | Yock . |
| 5,313,950 | 5/1994 | Ishikawa et al. . |
| 5,364,336 | 11/1994 | Carr . |
| 5,369,679 | 11/1994 | Sliski et al. . |
| 5,402,790 | 4/1995 | Jang et al. . |
| 5,414,748 | 5/1995 | Upadhya . |
| 5,422,678 | 8/1995 | Dinsmore et al. . |
| 5,422,926 | 6/1995 | Smith et al. . |
| 5,425,735 | 6/1995 | Rosen et al. . |
| 5,428,658 | 6/1995 | Oettinger et al. . |
| 5,437,277 | 8/1995 | Dumoulin et al. . |
| 5,444,254 | 8/1995 | Thomson . |
| 5,452,720 | 9/1995 | Smith et al. . |
| 5,454,809 | 10/1995 | Janssen . |
| 5,465,732 | 11/1995 | Abele . |
| 5,469,490 | 11/1995 | Golden et al. . |
| 5,474,075 | 12/1995 | Goldberg et al. . |
| 5,503,613 | 4/1996 | Weinberger . |
| 5,504,799 | 4/1996 | Suzuki . |
| 5,509,045 | 4/1996 | Kautz .................................... 378/123 |
| 5,511,107 | 4/1996 | Sliski . |
| 5,528,652 | 6/1996 | Smith et al. . |
| 5,566,221 | 10/1996 | Smith et al. . |
| 5,621,780 | 4/1997 | Smith et al. . |
| 5,623,139 | 4/1997 | Sliski . |
| 5,635,709 | 6/1997 | Sliski et al. . |
| 5,748,699 | 5/1998 | Smith ...................................... 378/65 |

OTHER PUBLICATIONS

Matsuda, et al., *Journal of Materials Science,* 23:509–514 (1988).

Papillon, *Diseases of the Colon & Rectum* 27(11): 695–700 (Nov. 1984).

Phillips, *Radiology,* 90(3):525–531 (Mar. 1968).

Sugiyama, et al., *Materials Science Forum,* 54&55:141–152 (1990).

Riege, *Nucl. Inst. and Meth. in Phys. Res.,* A340:80–89 (1994).

Schwartz, et al., *JACC,* 19(5):1106–1113 (Apr. 1992).

Soares, et al., *Nuclear Technology Publishing,* 47(174):367–372 (1993).

Strickland, *Clinical Radiology—The J. of the Faculty of Radiologists.* XVI(1–4):112–118 (Jan. to Oct. 1965).

Verin, et al., *Circulation,* 92:(8):2284–2290 (Oct. 1995).

Wang, et al., *Int. J. Radiation Oncology Biol. Phys.,* 9(8):1185–1189 (Aug. 1983).

Waksman, et al., *Circulation,* 92(6):1383–1386 (Sep. 1995).

Waksman, et al., *Circulation,* 92(10):3025–3031 (Nov. 1995).

Waksman, et al., *Circulation,* 91(5):1533–1539 (Mar. 1995).

Wiedermann, et al., *JACC,* 23(6):1491–1498 (May 1994).

Wiedermann, et al., *JACC,* 25(6):1451–1456 (May 1995).

Wiedermann, et al., "Effects of high–dose intracoronary irradiation on vasomotor function and smooth muscle histopathology", pp. H125–H132 (1994).

Brandes, George R., "Chapter 17—Diamond Vacuum Electronics," Advanced Technology Materials, (undated), pp. 1–27, no date.

Collins, C.B. et al., "Laser plasma source of amorphic diamond," Appl. Phys. Lett. 54(3), Jan. 16, 1989, pp. 216–218.

Davanloo, F. et al., "Amorphic diamond films produced by a laser plasma source," J. Appl. Phys. 67(4), Feb. 15, 1990, pp. 2081–2087.

Geis, M.W. et al., "Diamond emitters fabrication and theory," J. Vac. Sci. Technol. B 14(3), May/Jun. 1996, pp. 2060–2067.

Givargizov, E.I. et al., "Cold emission from the single–crystalline microparticle of diamond on a Si tip," J. Vac. Sci. Technol. B 14(3), May/Jun. 1996, pp. 2030–2033.

Himpsel, F.J. et al., "Quantum photoyield of diamond (111)—A stable negative–affinity emitter," Physical Review B, vol. 20, No. 2, Jul. 13, 1979, pp. 624–627.

Kumar, N. et al., "Diamond–based field emissionn flat panel displays," Solid State Technology, May, 1995, pp. 71–74.

Latham, R.V., "High Voltage Vacuum Insulation, Basic Concepts and Technological Practice," Dept. of Electronic Engineering and Applied Physics, Aston University, Birmingham, U.K., (undated) 5 pages.

Liu, J. et al., "Field emission characteristics of diamond coated silicon field emitters," J. Vac. Sci, Technol. B 13(2), Mar./Apr. 1995, pp. 422–426.

Pupeter, N. et al., "Field emission measurements with $\mu$m resolution on chemical–vapor–deposited polycrystalline diamond films," J. Vac. Sci. Technol. B 14(3), May/Jun. 1996, pp. 2056–2059.

Wagal, S.S., "Diamond–like carbon films prepared with a laser ion source," Appl. Phys. Lett. 53(3), Jul. 18, 1988, pp. 187–188.

Wang, C. et al., "Cold Field Emission From CVD Diamond Films Observed in Emission Electron Microscopy," Electronics Letters, vol. 27, No. 16, Aug. 1, 1991, pp. 1459–1461.

Xie, C. et al., "Electron Field Emission from Amorphic Diamond Thin Films," (undated), 2 pages.

Xu, N.S. et al., "A diagnostic study of the field emission characteristics of individual micro–emitters in CVD diamond films," J. Phys. D. Appl. Phys. 27 (1994) 1988–1991, 4 pages.

Zhirnov, V.V. et al., "Emission stability and high current performance of diamond–coated Si emitters," J. Vac. Sci. Technol. B 14(3), May/Jun. 1996, pp. 2034–2036.

MINIATURE X-RAY DEVICE HAVING COLD CATHODE

FIELD OF THE INVENTION

The present invention is directed to an x-ray device having a cold cathode and a method of fabrication, and more particularly to a miniature x-ray device having a cold cathode and method for fabrication for delivering radiation to vessels, lumen, or cavities of a body, such as cardiovascular tissue, to treat restenosis and other conditions.

BACKGROUND OF THE INVENTION

In the medical sciences, doctors and scientists continually strive to find less invasive ways to treat patients. By using treatments that are less intrusive to the body, doctors can greatly reduce the stress on the patient's system. For example, laparoscopic techniques enable physicians to explore the interior of the body and perform surgery through a small opening in the skin. Less intrusive medical techniques are extremely beneficial when applied to cardiovascular diseases, reflux disease of the esophagus, and other diseases of vessels, cavities and lumens of the body.

Cardiovascular diseases affect millions of people, often causing heart attacks and death. One common aspect of many cardiovascular diseases is stenosis, or the thickening of an artery or vein wall, decreasing blood flow through the vessel. Angioplasty procedures have been developed to reopen clogged arteries without resorting to a bypass operation. However, in a large percentage of cases, arteries become occluded again after an angioplasty procedure. This recurrent thickening of the vessel wall is restenosis. Restenosis frequently requires a second angioplasty and eventual bypass surgery. Bypass surgery is very stressful on the patient, requiring the chest to be opened, and presents risks from infection, anesthesia, and heart failure.

Effective methods of preventing or treating restenosis could benefit millions of people. One approach uses drug therapy to prevent or minimize restenosis. For example, Heparin has been used as an anticoagulant and an inhibitor of arterial smooth muscle proliferation. Dexamethasone is another drug which may prevent smooth muscle proliferation. It has been suggested that such anticoagulants and antiproliferative agents may be effective at preventing restenosis after an angioplasty procedure thereby eliminating the necessity to repeat the procedure.

To be most effective and to reduce the associated risk, it is desirable to deliver such drugs directly to the region to be treated. In order to minimize the invasiveness of the procedure, a drug delivery device that is adapted to traverse the human cardiovascular or circulatory system must be used. Such a device must be capable of entering small blood vessels with diameters of about two to four millimeters. Such a device must also be capable of making hairpin turns as it follows a tortuous path.

Many types of catheters have therefore been developed to deliver these and other effective drugs to the site of the restenosis. The major problem with local drug delivery is that the blood flow quickly washes away the drug so that only a small portion of the drug delivered is actually absorbed by the vessel wall. To address this problem, catheters frequently use pressure to drive the drug into the tissue or plaque, potentially causing damage to the lumen wall. Techniques of delivery which do not use pressure use occlusion balloons to isolate the area from blood flow to enable sufficient absorption of the medication. However, the blood flow in an artery can only be occluded for a limited period of time while the drug is delivered. Due to these and other problems, localized delivery of drugs is not able to achieve sufficient absorption in the treatment of restenosis.

Another treatment for restenosis that has been attempted is beta-irradiation of the vessel wall by positioning radioactive isotopes in the vessel at the site of the restenosis. However, the depth of the penetration of the radiation is impossible to control with this method. The depth of the penetration of the radiation is determined by the type of the radio-isotope used. The radioactive source will also irradiate other healthy parts of the body as it is brought to the site to be treated. Another disadvantage is that medical personnel must take extensive precautions when handling the radioactive material.

Less intrusive techniques are also extremely beneficial when applied to the esophagus. Tens of millions of Americans suffer from gastroesophageal reflux disease (GERD). GERD is characterized by a backward flow of the stomach and duodenal contents into the esophagus. These conditions result when the valve at the junction between the esophagus and the stomach does not function properly. When this occurs frequently, it is termed chronic GERD or reflux esophagitis. The symptoms of this condition are dyspepsia, or discomfort in the esophagus after meals, burning chest, upper abdominal pain, sour taste, and regurgitation.

Medical research has revealed that the acidic stomach contents cause anatomic abnormalities of the epithelium, or lining, of the esophagus during reflux. The cell type of the epithelium of the esophagus changes from a squamous, or circular-shaped cell, to a columnar, or rectangular-shaped, cell type. This cellular damage of the epithelium is termed Barrett's esophagus.

Barrett's esophagus is a precursor for cancer of the gastroesophageal system. Barrett's-associated malignancies strike approximately 10,000 people per year. There is a high rate of progression from reflux disease to Barrett's esophagus. In fact, 90 percent of patients with reflux symptoms who have an endoscopic examination show anatomic abnormalities of the epithelium.

Diagnosis of cancer in Barrett's esophagus ordinarily leads to removal of the diseased segment of the esophagus. However, an effective treatment of Barrett's disease could prevent the progression to cancer and could therefore reduce the need for this painful and drastic procedure. An effective treatment for Barrett's esophagus could improve the lives of many people. Ultrasound and argon-ion plasma treatments have been suggested to treat Barrett's esophagus, but these techniques are in early experimental stages and have not been proven effective. It is believed that photodynamic therapy is also a possibility.

Many other disorders could be treated with small, effective medical devices capable of accessing the interior of the body. For example, one disorder of the gastrointestinal system is pyloric strictures. Pyloric strictures occur in the pylorus, or distal aperture of the stomach. The pylorus is surrounded by a strong band of circular muscle, through which the stomach contents are emptied into the duodenum.

Pyloric strictures can be subjected to dilatation to open the pylorus passage. However, the pylorus frequently thickens in response to the dilatation. Repeated dilatation has been used to treat pyloric strictures, but has not proven to be an effective long-term solution. There is a need for treatments to prevent this recurrent thickening of the pylorus.

Thus, there is a need for miniature devices and effective methods to treat the interior of the body with minimal intrusion. Effective, less invasive techniques for treating stenosis and restenosis of a lumen, treating GERD, and treating pyloric strictures are especially needed.

SUMMARY OF THE INVENTION

A device is described suitable for inserting into a body and delivering x-ray radiation, comprising a connector, including a proximal and a distal portion, a vacuum housing coupled to the distal portion of the connector, an anode disposed within the vacuum housing, and a cathode disposed within the vacuum housing. The cathode has a granular surface and is operative with the anode and the connector to produce the x-ray radiation. The cathode is composed of a material that also allows it to act as a getter. The cathode may also include diamond material.

A method is described for producing a device suitable for insertion into a body and delivering x-ray radiation, comprising forming a cathode from granular getter material, and combining the cathode with an anode, a vacuum housing, and a connector, so that the cathode is operative with the anode and connector to produce x-ray radiation.

BRIEF DESCRIPTION OF THE DRAWINGS

The invention may be more completely understood in consideration of the detailed description of various embodiments of the invention which follows in connection with the accompanying drawings.

Figure 2:
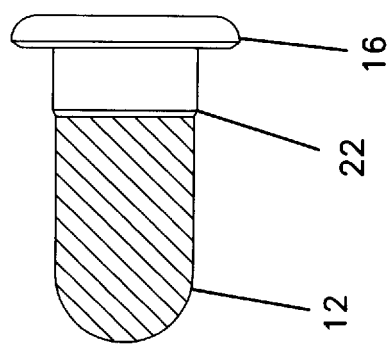
FIG. 2 shows a side view of one embodiment of a cathode and end cap of the x-ray device of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE VARIOUS EMBODIMENTS

The present invention is applicable to a variety of devices, and methods of fabrication thereof, which irradiate passages, lumens, vessels, cavities, or interior sites in a body with x-ray radiation. The invention is particularly advantageous in treating restenosis and stenosis of the cardiovascular vessels, gastroesophageal and gastrointestinal systems, and other ailments where delivery of localized x-ray radiation to interior portions of the body has been discovered to be effective. While the present invention is not so limited, an appreciation of various aspects of the invention is best gained through a discussion of application examples operating in such environments.

The present invention is related to the following two copending applications: "Device for Delivering Localized X-Ray Radiation to an Interior of a Body and Method of Manufacture," Ser. No. 08/806,244, filed Feb. 21, 1997; and "X-Ray Catheter," Ser. No. 08/701,764, filed Aug. 22, 1996. These two copending applications are hereby incorporated by reference in their entirety.

Many disease states of the body involve the abnormal thickening of a lumen or passage. The inventors have found that the x-ray device of the present invention provides a very promising way to treat these types of conditions. The x-ray device produces ionizing radiation that penetrates to the first layers of cells on the surface of the passage or lumen. This radiation induces apoptosis, or programmed cell death.

Apoptosis differs from another type of cell death, necrosis. In apoptosis, a disruption in the gene structure of the cell results in the cell failing to replicate, and in some cells, results in an induced cell death where the contents of the cell are utilized by adjacent cells. Cell death by apoptosis therefore reduces inflammation and the biochemical results of inflammation, as compared to necrosis, which results in scarring and thickening of the surface cells.

X-ray radiation has been found to reduce the occurrence of restenosis when x-ray radiation is applied to area of a blood vessel where an angioplasty or other expansion of the vessel has taken place. In coronary applications, it is desirable to have the x-ray radiation penetrate into the adventitia tissue of the blood vessels about 2 mm deep. Penetration into the cardiac muscle tissue should be minimized. Further, it is desirable to deliver x-ray radiation with a peak energy of about 8–10 kiloelectron volts (keV) in coronary applications.

In one aspect of the present invention, an x-ray device positionable in the esophagus is used to treat Barrett's esophagus by inducing apoptosis in the abnormal cells of the epithelium. The use of the x-ray device of the present invention may therefore be used to reduce the escalation of this condition to cancer. Further, the x-ray device of the present invention may be used for preventing the thickening of the pylorus after dilatation of pyloric strictures.

When treating the interior of the body, it is desirable to use as small a device as possible. Very small devices are required when traversing the blood vessels of the cardiovascular system, for example. A smaller device will be more easily guided to the site of treatment. It is also important to minimize the occlusion of the blood vessel, in order to allow blood flow to the greatest extent possible.

Figure 1:
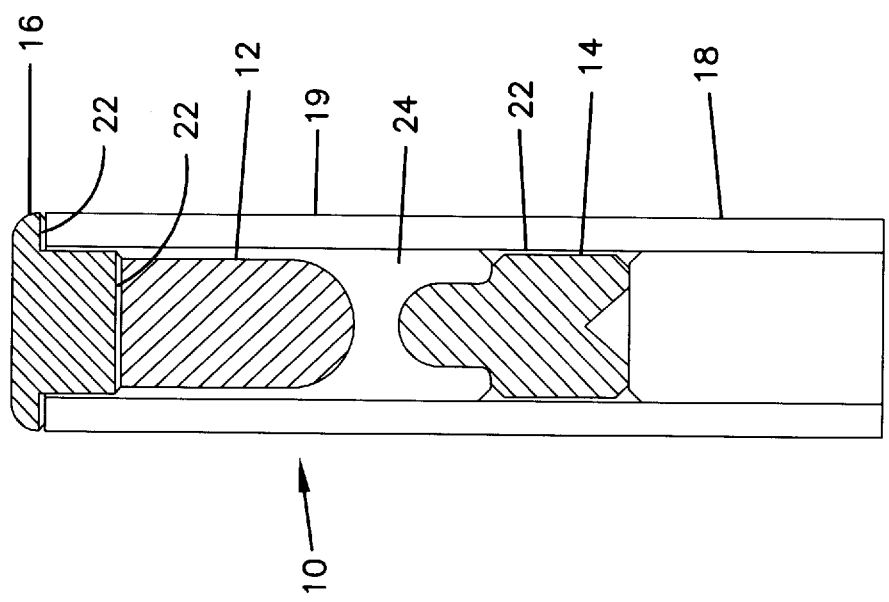
FIG. 1 shows a cross-sectional view of an embodiment of an x-ray emitter of the invention.

FIG. 1 illustrates an x-ray emitter of a first embodiment in which a cathode 12 of an x-ray emitter 10 comprises a getter.

An x-ray emitter, as shown in FIG. 1, includes a cathode 12, an anode 14, a housing shell 18, and an end cap 16. The anode 14, endcap 16, and shell 18 define a vacuum chamber which encloses a vacuum space 24. In order to produce x-ray radiation, an electrical field is applied across the cathode and anode, resulting in the emission of electrons from the cathode and acceleration of these electrons toward the anode. The anode 14 consists of a heavy metal that emits x-ray radiation when the high-speed electrons are incident upon the anode 14. The x-ray radiation is emitted from the anode 14 and travels through the shell 18 which is transparent to x-rays. The anode and cathode are separated by a gap that varies depending on the requirements of the particular application. For many coronary applications, the gap may range from 0.20 to 1.5 mm.

The x-ray emitter 10 may be supplied with a high voltage by a connector, not shown in FIG. 10. The x-ray emitter 10 may be coupled to the connector at a distal end, which is disposed within the body during treatment. A proximal end of the connector emerges from the body and may be coupled to a voltage generator.

It is desirable to maintain a vacuum condition within the shell 18. In order to create the vacuum, frequently, the components are assembled within a vacuum or the chamber is pumped out by conventional methods. Further, a getter may also be disposed within the housing. The getter has an activation temperature at which it will react with stray gas molecules in the vacuum. The getter eliminates stray gas molecules, improving the quality of the vacuum within the shell.

In accordance with this invention, a getter may serve as an electron emitter when a voltage differential is applied. Therefore, the getter may be used as the cathode. This combination of elements results in a smaller x-ray device with a very simple design.

While attempting to produce x-ray radiation of about 8–10 keV in the body, it is important to keep the magnitude of the electrical fields at the surface of the cathode low enough to prevent arcing between the anode and the cathode. Just on the other side of the housing shell 18 from the anode and cathode, a conductive layer 19 is held at ground. An electrical discharge from the surface of the cathode to the anode along the inside surface of the shell is termed an electric flashover. An electric flashover must be prevented to keep the x-ray emitter operative. According to the present invention, as a weaker electrical field at the cathode surface is required for cold electron emission, the danger of electric flashover is reduced.

Because of concerns about flashover, dielectric strength should be considered when choosing a material for the housing. The dielectric strength is the maximum electric field that a material can withstand before breaking down. However, surface discharge may occur at lower electrical field strengths. Many individual factors may affect the flashover voltage, such as the surface geometry, material contamination, the material history, and vacuum quality.

It is possible to have a safety switch mechanism that monitors power output to detect the occurrence of flashover. If flashover occurs, all remaining electrostatic energy in the cable may be quickly transferred to a resistor in the high voltage source outside the body.

The ability to lower the required electric field at the cathode results in a less expensive manufacturing technique. Small irregularities on the surface of the cathode result in an increase in the magnitude of the electrical field for an applied voltage, thereby increasing the chance of electrical flashover. The weaker the required electrical field at the cathode, the more imperfections can be tolerated on the cathode surface without risking flashover.

According to the invention, a cathode made of granular metal materials may not require an additional coating, such as diamond, in order to emit electrons at moderate electrical fields for x-ray applications. The granulated surface of the cathode provides multiple microprotrusions capable of efficient field emission of electrons at moderate electrical fields. Therefore, in accordance with the invention, the cathode consists of granular getter materials. Using granular getter materials, field emission current densities of approximately 0.5–5 milliamps per square millimeter are observed at the cathode at electrical fields of 10–50 volts per micron. This level of emission current is similar to that found in diamond-coated cathodes at electrical fields that are moderate for x-ray production. However, a device using a granular getter material as the cathode is considerably less complicated to manufacture. The cathode with microprotrusions may be formed by thermal diffusion bonding of granulated getter material, or getter powder, having granular sizes of 0.5 to 50 micrometers in diameter.

In accordance with one embodiment of the invention, x-ray radiation is produced while keeping the required electrical fields low by mixing diamond powder with the granulated getter materials before forming the cathode of the present invention. Diamond materials display valuable properties as field emitters, losing electrons easily as a field is applied. Where a diamond powder is included in the cathode, an electrical field of 10–50 volts per micron will produce current densities in the range of 1–10 milliamps per millimeter square.

The diamond material may be purchased commercially from numerous sources. Most of the powder diamond material is obtained from CVD processes, although it may be produced from natural beds of diamond.

Heat is generated by the operation of the x-ray emitter of the present invention. Therefore, it is important that coefficients of thermal expansion (CTE) are similar in all materials used to construct the x-ray emitter. If materials are used having inconsistent CTEs, then the integrity of the vacuum chamber of the x-ray emitter may be jeopardized. In one embodiment of the invention, the end cap 16 is composed of molybdenum, having a CTE of $4.9 \times 10^{-6 \circ} \text{ C}^{-1}$. The shell 18 of the x-ray emitter may be composed of isotropic boron nitride having a CTE of $3.8 \times 10^{-6 \circ} \text{ C}^{-1}$. The CTE of the anode is also important because it seals the end of the shell 18 closest to the coaxial cable. The anode may be comprised of tungsten, having a CTE of $4.6 \times 10^{-6 \circ} \text{ C}^{-1}$.

Another consequence of heat generation is that cooling may be desirable in some situations. Where the x-ray emitter of the present invention is used in a blood vessel, the blood flow past the emitter is sufficient to dissipate the generated heat. Where the device is used in the esophagus or other cavity, a fluid could circulate through a balloon surrounding the emitter to prevent damage to the body.

Now referring to FIG. 2, the end cap of the x-ray emitter is shown from a side view. In one embodiment, the elements of the x-ray emitter may be bonded together using vacuum brazing. The brazing alloy 22 joins the cathode to the end cap. Further brazed alloy connects the end cap to the shell. Additional brazing alloy may bond the anode to the shell, shown in FIG. 1. The vacuum brazing techniques are important to maintaining the integrity of the vacuum chamber 24. Vacuum brazing as used in the x-ray emitter of the present invention may be provided by Koral Labs, Minneapolis, Minn., for example. Two examples of preferred brazing alloys are AuSn and AuGe.

The getter cathode 12 may be composed of many different types of getter materials. The getter may include zirconium, aluminum, vanadium, iron, and/or titanium. In one embodiment, the getter materials may be composed of an alloy including vanadium, iron and zirconium. One successful choice for the getter cathode is a material produced SAES and referred to as ST707. Getter alloy ST707 is produced by thermal diffusion bonding and is composed of 24.6% vanadium, 5.4% iron, and 70% zirconium.

The getter will be sufficiently conductive and capable of electron emission to serve as an effective cathode at moderate electrical fields, for example, 10 volts per micron to 60 volts per micron. Before the getter is activated, it is covered with a layer of oxidation that shields the getter material from the atmosphere at normal conditions. When the getter is heated to an activation temperature in a vacuum, the oxidation layer diffuses into the interior of the getter, revealing the active getter surface, which will react and bond with any molecules. Under vacuum conditions, the active getter surface reacts with any stray gas molecules and bonds them to the getter, thereby improving the quality of the vacuum. The SAES ST707 alloy getter has an activation temperature of 400–500° C.

Figure 3:
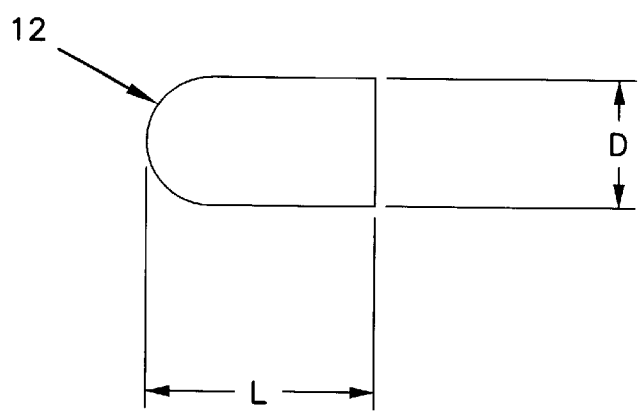
FIG. 3 shows a cross-sectional view of a cathode of an embodiment of the x-ray device of the present invention.
Figure 4:
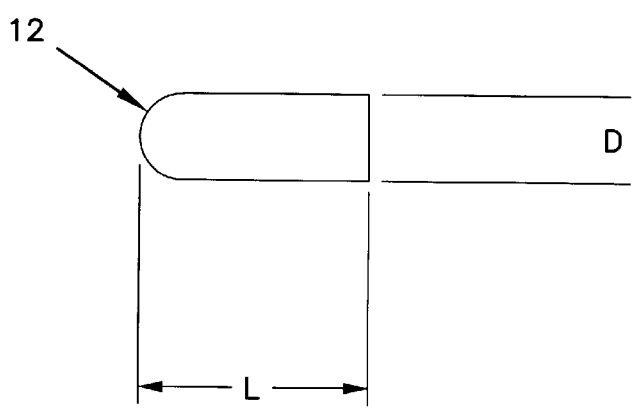
FIG. 4 shows a cross-sectional view of a cathode used in another embodiment of the x-ray device of the invention.

The shape of the cathode affects the electron emission qualities of the cathode. FIG. 3 shows a cross-sectional view of the cathode shown in FIGS. 1 and 2. This cathode is cylindrically shaped with a half full sphere shape on one end. The diameter D is 0.75 mm. The length of the cathode L is 1.30 mm. A smaller catheter where D is 0.50 mm and L is 1.30 mm is shown at FIG. 4.

Figure 5:
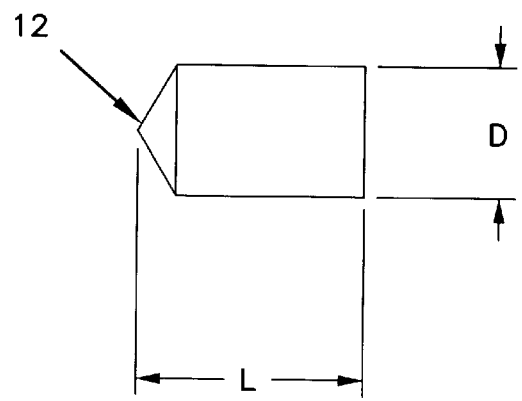
FIG. 5 shows a cross-sectional view of a cathode of another embodiment of the x-ray device of the invention.

FIG. 5 illustrates a cathode 12 having a standard 118° drill point tip. For the cathode 12 shown in FIG. 5, D is 0.75 mm and L is 1.30 mm.

Figure 6:
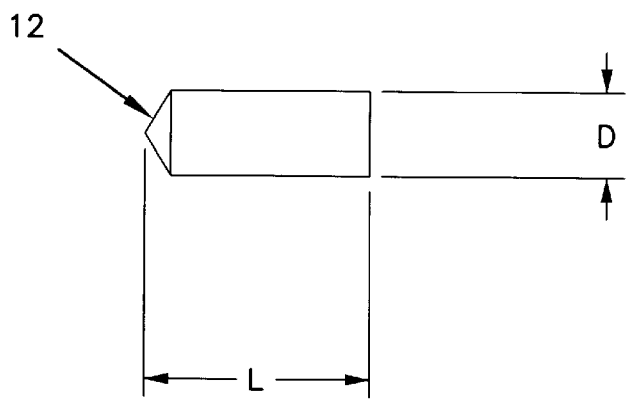
FIG. 6 shows a cross-sectional view of a cathode of another embodiment of the x-ray device of the invention.

FIG. 6 shows a smaller cathode in the standard 118° drill point tip configuration. In FIG. 6, D is 0.50 mm and L is 1.30 mm.

Figure 7:
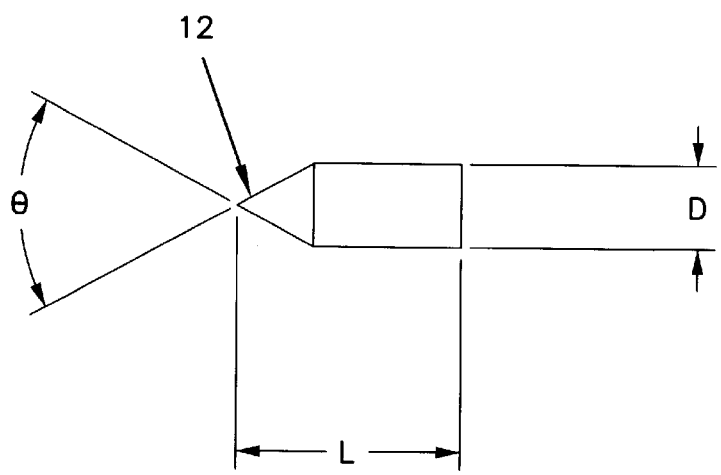
FIG. 7 shows a cross-sectional view of a cathode of an additional embodiment of the x-ray device of the invention.

FIG. 7 shows a cathode 12 having a sharp point. The angle $\Theta$ is 60°. For the cathode shown in FIG. 7, D is 0.50 mm and L is 1.30 mm.

Figure 8:
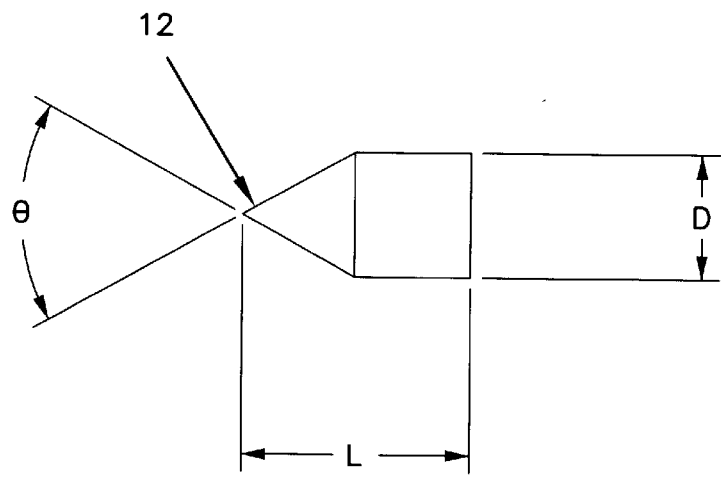
FIG. 8 shows a cross-sectional view of a cathode of another embodiment of the x-ray device of the invention.

The cathode shown in FIG. 8 is also a sharp point configuration where $\Theta$ is 60°. The diameter D is 0.75 mm while the length L is 1.30 mm.

In order to apply an electric field across the anode and cathode, a coaxial cable, not shown in the figures, may be used as the connector. The coaxial cable may be coupled to a high-voltage generator at a proximal end that remains outside the body. At the distal end, the coaxial cable may be coupled to the x-ray emitter. An internal conductor of the coaxial cable may be coupled to the anode at the appropriate voltage. An external conductive layer of the coaxial cable may be held at ground and coupled to the cathode base via a conductive solder. Other known methods may also be used to apply the electric field across the anode and cathode.

The coaxial cable used in conjunction with the present invention must be able to carry the required voltages, have sufficient flexibility to make sharp turns as it follows the path of an interior passage of the body, and have a sufficiently small diameter to traverse the area of the body to be treated. Standard high voltage coaxial cables are generally not flexible enough. However, the inventors have found that miniature high frequency coaxial cables with an outer diameter of approximately 1.0 millimeter to 3.0 millimeters are available which also exhibit sufficient flexibility. These types of cables are typically used in high frequency applications at voltages less than several kilovolts (kV). In connection with the present invention, the inventors have discovered that such cables can hold direct current voltages as high as 75–100 kV without breakdown. Therefore, these cables are well suited for use with the x-ray device of the present invention. In one embodiment, a cable with an outer diameter less than or equal to 3.0 millimeters is used. In another embodiment, the cable has an outer diameter of 1–2 millimeters. Such cables are manufactured by, for example, New England Electric Wire Corporation, Lisborn, N.H.

The shell 18 of the x-ray emitter may be substantially transparent to x-rays in order to allow the full dosage to reach the treatment site. The shell may also be an electrical insulator, capable of supporting the x-ray emitter without electrical discharge between the exterior of the shell at ground and the interior of the shell at high voltage. The shell may be comprised of chemical vapor deposition (CVD) boron nitride, CVD silicon nitride, beryllium oxide, aluminum oxide, or other ceramic material. The shell may also be composed of a CVD diamond three-dimensional structure.

In one embodiment of the invention, the field emission properties of the cathode may be modified by a conditioning procedure that alters the surface of the cathode to achieve predetermined field emission parameters. Multiple applications of high voltage are carried out at different distances and relative positions of the electrodes, causing electrical discharges between electrodes. The discharges destroy unstable emitting sites at the cathode surface and drive the field emission parameters into the desired range. As a result, a conditioned cathode is capable of more efficient and consistent performance. Conditioning of the cathode may be carried out according to the concepts set forth in *High Voltage Vacuum Insulation: Basic Concepts and Technological Practice*, R. V. Latham, Editor, Academic Press, 1995, which is incorporated by reference herein in its entirety.

Spark conditioning and current conditioning may be used to improve a cathode in one embodiment of the present invention. The slow application of voltage involved in current conditioning may be the most preferable method for conditioning the cathode of the present invention. Current conditioning involves slow increases in the application of voltage across the cathode and an anode. Voltage application may begin at about 1 kilovolt per millimeter and gradually increase to about 60 kilovolts per millimeter, and perhaps as high as 100 kilovolts per millimeter. The voltage application may increase in increments of 1 kilovolt per millimeter in one embodiment of the present invention. The procedure for conditioning one cathode may take about thirty minutes. The conditioning process may be carried out before the cathode is assembled with the housing.

The slow application of increasing voltage gradually melts the microprotrusions present on the cathode. The sharpest field-emitting microprotrusions may be thermally blunted following excessive electron emission brought on by the current conditioning.

A method for producing a device suitable for insertion into a body and delivering x-ray radiation is also contemplated by the invention. First, a cathode structure including molded granular getter material is provided. The cathode and an anode are then enclosed in a vacuum housing so that the cathode is operative with the anode to produce x-ray radiation. This method of manufacture provides the advantage of simplicity because the cathode and getter components are present in the same structure.

The various embodiments described above are provided by way of illustration only and should not be construed to limit the invention. Those skilled in the art will readily recognize various modifications and changes which may be made to the present invention without strictly following the exemplary embodiments and applications illustrated and described herein, and without departing from the true spirit and scope of the present invention which is set forth in the following claims.

We claim:

1. A device suitable for insertion into a body and for delivery of x-ray radiation, comprising:

a connector, including a proximal and a distal portion;

a vacuum housing coupled to the distal portion of the connector;

an anode disposed within the vacuum housing; and a cathode disposed within the vacuum housing and having a granular surface, the cathode being operative with the anode and the connector to produce the x-ray radiation, the cathode being composed of a material that also allows it to act as a getter.

2. The device of claim 1, wherein the granular surface of the cathode provides multiple protrusions capable of field emission of electrons when a moderate electrical field for x-rays is applied to the cathode.

3. The device of claim 1, wherein the cathode is formed from a granular material including granular sizes in a range of about 0.5 to 50 micrometers.

4. The device of claim 1, wherein the cathode is formed by thermal diffusion bonding of a granular getter material.

5. The device of claim 1, wherein the anode and the cathode are separated by a distance ranging from about 0.2 to 1.5 millimeters.

6. The device of claim 1, wherein the vacuum housing has a center axis and the anode is positioned coaxially with the center axis.

7. The device of claim 1, wherein the connector is a flexible conductor.

8. The device of claim 1, wherein the connector is a flexible coaxial cable.

9. The device of claim 1, wherein the cathode is comprised of an alloy including zirconium and aluminum.

10. The device of claim 1, wherein the cathode is comprised of a vanadium alloy.

11. The device of claim 1, wherein the cathode is comprised of an iron alloy.

12. The device of claim 1, wherein the cathode is comprised of titanium.

13. The device of claim 1, wherein the cathode is comprised of aluminum.

14. The device of claim 1, wherein the cathode is comprised of an alloy including vanadium, iron and zirconium.

15. The device of claim 1, wherein the cathode is prepared by a conditioning process that reduces unstable emission sites at the cathode surface.

16. A device suitable for insertion into a body and for delivery of x-ray radiation, comprising:

a connector, including a proximal and a distal portion;

a vacuum housing coupled to the distal portion of the connector;

an anode disposed within the vacuum housing; and a cathode disposed within the vacuum housing and having a granular surface, the cathode being operative with the anode and the connector to produce the x-ray radiation, the cathode being comprised of a material that also allows it to act as a getter and containing diamond powder mixed with a getter material.

17. The device of claim 16, wherein the granular surface of the cathode provides multiple protrusions capable of field emission of electrons when a moderate electrical field for x-rays is applied to the cathode.

18. A method for producing a device suitable for insertion into a body and delivering x-ray radiation, comprising:

forming a cathode from granular getter material; and combining the cathode with an anode, a vacuum housing, and a connector, so that the cathode is operative with the anode and connector to produce x-ray radiation.

* * * * *